United States Patent
Singh et al.

(10) Patent No.: US 10,898,444 B2
(45) Date of Patent: Jan. 26, 2021

(54) EXTENDED RELEASE MULTIPARTICULATES OF RANOLAZINE

(71) Applicant: Sun Pharmaceutical Industries, Ltd., Mumbai (IN)

(72) Inventors: Harinder Singh, Kangra (IN); Shavej Ahmad, Uttar Pradesh (IN); Romi B. Singh, Benares (IN)

(73) Assignee: Sun Pharmaceutical Industries Limited, Mumbai (IN)

( * ) Notice: Subject to any disclaimer, the term of this patent is extended or adjusted under 35 U.S.C. 154(b) by 0 days.

(21) Appl. No.: 15/879,246

(22) Filed: Jan. 24, 2018

(65) Prior Publication Data
US 2018/0344653 A1    Dec. 6, 2018

(30) Foreign Application Priority Data

Jun. 1, 2017 (IN) .............................. 201711019271

(51) Int. Cl.
*A61K 9/50* (2006.01)
*A61K 31/495* (2006.01)

(52) U.S. Cl.
CPC .......... *A61K 9/5078* (2013.01); *A61K 9/5015* (2013.01); *A61K 9/5026* (2013.01); *A61K 9/5042* (2013.01); *A61K 31/495* (2013.01)

(58) Field of Classification Search
CPC .. A61K 9/5078; A61K 9/5015; A61K 9/5042; A61K 31/495; A61K 9/5026
See application file for complete search history.

(56) References Cited

U.S. PATENT DOCUMENTS

| | | | | |
|---|---|---|---|---|
| 6,525,057 B2 * | 2/2003 | Wolff | ................... | A61K 9/2027 514/252.1 |
| 6,562,826 B1 | 5/2003 | Wolff | | |
| 6,617,328 B2 | 9/2003 | Wolff et al. | | |
| 6,620,814 B2 | 9/2003 | Wolff et al. | | |
| 6,852,724 B2 | 2/2005 | Wolff | | |
| 6,864,258 B2 | 3/2005 | Wolff | | |
| 8,901,128 B2 | 12/2014 | Bhasale et al. | | |
| 2011/0151258 A1 * | 6/2011 | Anumula | ............. | C07D 295/15 428/402 |
| 2012/0039999 A1 * | 2/2012 | Chatterji | .............. | A61K 9/1635 424/456 |
| 2015/0037410 A1 * | 2/2015 | Gerber | ................... | A61K 47/38 424/472 |
| 2016/0271070 A1 * | 9/2016 | Singh | ................... | A61K 9/5078 |

FOREIGN PATENT DOCUMENTS

| | | | |
|---|---|---|---|
| CN | 103751112 | * | 4/2014 |
| CN | 103761112 A | | 4/2014 |

OTHER PUBLICATIONS

Colorcon—Surelease General Product Information v3—Feb. 2016 (Year: 2016).*
Ranexa Prescribing Information—Jan. 2016 (Year: 2016).*
Eudragit L30 D technical information—May 2014 (Year: 2014).*
CN 101066254 English translatiopn by Espacnet 2008.*
CN 103751112 English Translation by Espacnet 2014.*
Murthy et al, Formulation and evaluation of ranoilazine extended release tablets: Influence of polymers, Asian Journal of pharmaceutics, Jul. 2011, pp. 162-166.*
Extended European Search Report issued in EP Application No. 18174971.4, dated Oct. 31, 2018.
Gu Q, et al. "Ranolazine slow-released micro pellet inclused Ranolazine and officinal assistant material", WPI/THOMSON vol. 2008, No. 36, Nov. 7, 2001.

* cited by examiner

*Primary Examiner* — Mina Haghighatian
(74) *Attorney, Agent, or Firm* — Goodwin Procter LLP

(57) ABSTRACT

The present invention relates to an extended release multiparticulate composition comprising a plurality of discrete units, each discrete unit comprising ranolazine or a pharmaceutically acceptable salt thereof and one or more pharmaceutically acceptable excipients. The said multiparticulate composition is sprinkled onto soft foods or liquids for oral administration. Further, the multiparticulate composition is bioequivalent to the marketed extended release tablet. It further relates to a process of preparation of said multiparticulate composition and method of treatment of patients suffering from angina by administering said composition.

9 Claims, No Drawings

EXTENDED RELEASE MULTIPARTICULATES OF RANOLAZINE

RELATED APPLICATIONS

This application claims priority to and the benefit of Indian Application No. 201711019271, filed on Jun. 1, 2017, which is incorporated by reference in its entirety.

FIELD OF THE INVENTION

The present invention relates to an extended release multiparticulate composition comprising a plurality of discrete units, each discrete unit comprising ranolazine or a pharmaceutically acceptable salt thereof and one or more pharmaceutically acceptable excipients, wherein said multiparticulate composition is sprinkled onto soft foods or liquids for oral administration. Further, the said multiparticulate composition is bioequivalent to the marketed extended release tablet formulation of ranolazine. It also relates to a process of preparation of said multiparticulate composition and method of treatment of patients suffering from angina by administering said composition.

BACKGROUND OF THE INVENTION

Ranolazine, a piperazine derivative drug, is indicated for the treatment of chronic angina. It may be used concomitantly with β-blockers, nitrates, calcium channel blockers, antiplatelet therapy, lipid-lowering therapy, ACE inhibitors, and angiotensin receptor blockers.

Ranolazine has a relatively high solubility in lower pH and a short plasma half-life. This results in rapid drug absorption and clearance, causing undesirable fluctuations in plasma concentration of ranolazine and requires more frequent administration for adequate treatment.

Ranolazine is commercially available as film-coated extended release tablets and is marketed under the brand name Ranexa®.

U.S. Pat. No. 6,303,607 covers the marketed product and discloses a sustained release ranolazine formulation that is in the form of compressed tablets comprising an intimate mixture of ranolazine and a partially neutralized pH dependent binder that controls the rate of ranolazine dissolution in aqueous media across the range of pH in the stomach and in the intestine However, the commercially available extended release tablet formulation is not suitable for patients having dysphagia or difficulty in swallowing (such as geriatric patients). The available formulation should not be crushed as drug release will be compromised. The dosage and administration section of Ranexa® prescribing information states, "Ranexa® tablets should be swallowed whole and not crushed, broken, or chewed." The prescribing information of Ranexa® further warns against its use as sprinkle dosage form. Also, due to high dose the tablet size is bigger, leading to poor patient compliance.

Thus, there exists a need in the art to formulate a composition of ranolazine which provides compliance for the patients having dysphagia or difficulty in swallowing. One alternative is to prepare a sprinkle dosage form of ranolazine which is in the form of multiparticulates comprising a plurality of discrete units.

SUMMARY OF THE INVENTION

The present inventors have challengeably prepared a multiparticulate composition of ranolazine which is substantially free of immediate release component and is bioequivalent to the marketed extended release tablet formulation. The said multiparticulate composition is sprinkled onto soft foods or liquids to ease the administration with minimal or no impact on the bioavailability of ranolazine. The present invention would provide advantage for the patients who have difficulty in swallowing the conventional solid dosage forms like tablets or capsules.

The present invention relates to an extended release multiparticulate composition comprising a plurality of discrete units, each discrete unit comprising ranolazine or a pharmaceutically acceptable salt thereof and one or more pharmaceutically acceptable excipients, which is sprinkled onto soft foods or liquids for oral administration.

The inventors of the present invention found that release profile or stability is not affected by sprinkling the multiparticulate composition of ranolazine onto soft foods or liquids. The integrity of the coating is not influenced by longer exposure to soft foods or liquids. Moreover, the said multiparticulate composition can be administered through a feeding tube in a long term care setting to critically ill patients by dispersing in an aqueous media before administration.

DETAILED DESCRIPTION OF THE INVENTION

A first aspect of the present invention provides an extended release multiparticulate composition comprising a plurality of discrete units, each discrete unit comprising ranolazine or a pharmaceutically acceptable salt thereof and one or more pharmaceutically acceptable excipients, wherein said multiparticulate composition is sprinkled onto soft foods or liquids for oral administration.

In second aspect of the invention, there is provided an extended release multiparticulate composition comprising a plurality of discrete units, each discrete unit comprises ranolazine and one or more pharmaceutically acceptable excipients, wherein said multiparticulate composition releases about 15 to about 40% of ranolazine in initial 2 hours in 900 ml 0.1N HCl and about 60 to about 90% of the ranolazine in 6 hours in 900 ml pH 6.8 phosphate buffer; when measured in United States Pharmacopoeia (USP) type II dissolution apparatus, rotating at 50 rpm at a temperature of 37° C.

According to one of the embodiments of this aspect, the multiparticulate composition releases about 20 to about 35% of ranolazine in initial 2 hours in 900 ml 0.1N HCl.

According to another embodiment of above aspect, the multiparticulate composition releases about 25% to about 35% of ranolazine in initial 2 hours in 900 ml 0.1N HCl.

The term "ranolazine" comprises ranolazine base and pharmaceutically acceptable salts thereof, including hydrates and solvates thereof, and crystalline or amorphous forms thereof.

The term "pharmaceutically acceptable salts" include, but not limited to, salts formed with inorganic acids for example hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, menthanesulfonic acid, ethanesulfonic acid, p-toluenesulfonic acid and salicylic acid.

According to another embodiment of this aspect, the discrete units are in a form selected from the group consisting of pellets, granules, particles, mini-tablets and beads.

According to another embodiment of this aspect, the discrete units comprise a core and a coating.

According to another embodiment of this aspect, the core comprises ranolazine.

According to another embodiment of this aspect, the inert core has a $d_{90}$ particle size of about 0.08 mm to about 0.30 mm as determined using a Malvern particle size analyzer.

The "inert core" as used herein may be water-soluble, water-swellable, or water-insoluble. Examples of water-swellable cores include microcrystalline cellulose spheres such as Celltes and Celphere®. Examples of water-soluble cores include sugar spheres made of glucose, mannitol, lactose, xylitol, dextrose, or sucrose. Examples of water-insoluble cores include glass beads or silicon dioxide beads.

According to another embodiment of this aspect, the drug layer is present in an amount of about 60 to about 95% by total weight of the multiparticulate composition.

According to another embodiment of this aspect, ranolazine is present in an amount of about 60 to about 80%, by weight of drug layer.

According to another embodiment of this aspect, ranolazine is present in an amount of about 60 to about 70% by weight of drug layer.

According to another embodiment of this aspect, ranolazine is present in an amount of about 50 to about 70% by weight of drug layer.

According to another embodiment of this aspect, the discrete unit of a multiparticulate composition comprises an inert core coated with a drug layer comprising ranolazine and one or more pharmaceutically acceptable excipients, wherein the drug layer is further coated with a functional or non-functional coating.

According to another embodiment of this aspect, the drug layered core is coated by a functional coating layer comprising an extended release coating layer.

According to another embodiment of this aspect, the functional coating comprises an extended release polymer coating in an amount of about 1 to about 50% of the total weight of multiparticulate composition.

According to another embodiment of this aspect, the functional coating comprises an extended release polymer coating in an amount of about 5% to about 15% of the total weight of multiparticulates.

According to another embodiment of this aspect, the extended release polymer coating comprises a combination of a water-insoluble polymer and a pH-dependent polymer.

According to another embodiment of this aspect, the water-insoluble polymer and pH-dependent polymer in the coating layer are present in a weight ratio of from about 1:2 to 1:3.

According to another embodiment of this aspect, the extended release polymer coating further comprises a water-swellable polymer.

The term "water-soluble or swellable polymers" as used herein includes hydroxypropyl methyl cellulose, hydroxyethyl cellulose, polyethylene glycol, poly (ethylene oxide), hydroxypropyl cellulose, carboxymethyl cellulose, polyvinyl pyrrolidone, xanthan gum, starch, polyvinyl alcohol and mixtures thereof.

The term "water-insoluble polymers" as used herein includes cellulose ethers such as ethyl cellulose; cellulose esters, polymethacrylic acid esters copolymers, e.g., Eudragit® NE 30 D, and Eudragit® NE 40 D aminoalkyl methacrylate copolymers, e.g., Eudragit® RL 100, Eudragit® RL PO, Eudragit® RS PO, and Eudragit® RS 100; polyvinyl acetate, copolymers of polyvinyl acetate and polyvinyl pyrrolidone, and mixtures thereof. Preferably, the water-insoluble polymer is ethyl cellulose.

The term "pH-dependent polymers" as used herein includes acrylic acid derivatives e.g. methyl acrylate acrylic acid copolymer, methyl acrylate methacrylic acid copolymer, butyl acrylate styrene acrylic acid copolymer, methacrylic acid methyl methacrylate copolymer (e.g. Tradenames: Eudragit L 100 and Eudragit S, available from Rohm Pharma), methacrylic acid ethyl acrylate copolymer e.g. Eudragit L 100-55, available from Rohm Pharma, methyl acrylate methacrylic acid octyl acrylate copolymer; cellulose derivatives e.g. hydroxypropylmethylcellulose acetate succinate, hydroxypropylmethylcellulose phthalate, hydroxymethylethylcellulose phthalate, cellulose acetate phthalate, cellulose acetate succinate, cellulose acetate maleate, cellulose acetate trimelliate cellulose benzoate phthalate, cellulose propionate phthalate, methylcellulose phthalate, carboxymethylethylcellulose, ethylhydroxyethylcellulose phthalate, polyvinyl derivatives e.g. polyvinyl alcohol phthalate, polyvinylacetal phthalate, polyvinyl butylate phthalate, polyvinylacetoacetal phthalate & maleic acid copolymers or mixtures thereof.

A third aspect of the present invention provides an extended release multiparticulate composition comprising a plurality of discrete units, each discrete unit comprises
a) a core comprising ranolazine and
b) a coating layer comprising an extended release polymer layer comprising a water-insoluble polymer and a pH-dependent polymer; wherein ranolazine is present in the composition in an amount of about 1000 mg.

According to one of the embodiments of this aspect, the multiparticulate composition is bioequivalent to the marketed extended release tablet of ranolazine when administered to the human subjects in fasting and fed states.

According to another embodiment of this aspect, the ranolazine is present in the discrete unit in an amount of about 40 to about 85% by total weight of the multiparticulate composition.

According to another embodiment of this aspect, the ranolazine is present in an amount of about 50 to about 70% by total weight of the multiparticulate composition.

According to another embodiment of this aspect, the ranolazine is present in an amount of about 55 to about 69% by total weight of the multiparticulate composition.

According to another embodiment of this aspect, the extended release polymer coating further comprises a plasticizer.

According to another embodiment of this aspect, the plasticizer is water insoluble.

Examples of plasticizers include tributyl citrate, dibutyl sebacate, acetyl tributyl citrate, glyceryl monostearate, diethyl phthalate, castor oil, acetylated monoglycerides, diacetylated monoglycerides, cetyl alcohol, and mixtures thereof.

The addition of plasticizer in the present invention helps to maintain integrity of coating layer while achieving desired rate of release of ranolazine from multiparticulates.

A fourth aspect of the present invention provides an extended release multiparticulate composition comprising a plurality of discrete units, each discrete unit comprises:
a) a core comprising ranolazine,
b) a coating layer comprising an extended release polymer layer comprising a water-insoluble polymer and a pH-dependent polymer to form coated cores, and c) an optional coating of a top coat over the coated cores of step (b).

According to one of the embodiments of this aspect, said top coat is present in amount of about 5% to about 35%, by weight of multiparticulate composition.

According to another embodiment of this aspect, said top coat is present in amount of about 5% to about 15% by weight of multiparticulate composition.

According to another embodiment of this aspect, said top coat comprises pH dependent polymers having a solubility below pH 5.5 Examples of top coat polymers include poly(meth)acrylic acid esters copolymers (e.g Eudragit™).

According to another embodiment of above aspects, the multiparticulate composition is substantially free of any microenvironment regulating agent.

The term "substantially free" means that multiparticulate composition contains less than 0.1% of microenvironment regulating agent.

According to another embodiment of this aspect, the microenvironment regulating agent is sodium hydroxide.

According to another embodiment of this aspect, the multiparticulate composition is sprinkled onto soft foods or liquids.

According to another embodiment of this aspect, the multiparticulate composition is sprinkled onto soft foods for example, applesauce, yogurt, cottage cheese, peaches purees, pears purees, lychee purees, apricots purees, grapes purees, strawberries purees, raspberries purees, and bananas purees at the time of administration.

According to another embodiment of this aspect, the multiparticulate composition is sprinkled onto liquids, for example, cranberry juice, grape fruit juice, orange juice, pineapple juice, mango juice, apple juice, vegetable juice, tomatoes juice, water and milk at the time of administration.

According to yet another embodiment of this aspect, the multiparticulate composition when sprinkled onto soft foods or liquids are stable for at least about 15 minutes without affecting the stability of the extended release coating.

According to yet another embodiment of this aspect, the multiparticulate composition when sprinkled onto soft foods or liquids are stable to be administered immediately with soft food.

According to another embodiment of this aspect, the multiparticulate composition is suitable for administration to a patient via a feeding tube.

According to another embodiment of this aspect, the feeding tube is NG tube or G tube.

According to another embodiment of this aspect, the multiparticulate dispersion in an aqueous media is stable when administered in a feeding tube after holding for at least 10 minutes.

According to another embodiment of this aspect, the multiparticulate composition is substantially free of immediate release component.

The term "substantially free" as used herein means that multiparticulate composition contains less than 30% of immediate release component.

The term "immediate release" as used herein refers to the multiparticulate composition that release at least 80% of the active agent within 1 hour.

According to another embodiment of this aspect, the multiparticulate composition when administered to healthy subjects under fasting conditions provide a mean $C_{max}$ value in the range of about 0.9 to about 2.9 ng/mL/mg.

According to another embodiment of this aspect, multiparticulate composition when administered to healthy subjects under fasting conditions provide a mean $AUC_{0-t}$ value in the range of about 14.7 to about 50 ng·hr/mL/mg.

According to another embodiment of this aspect, the multiparticulate composition when administered to healthy subjects under fed conditions provide a mean $C_{max}$ value in the range of about 1 to about 5 ng/mL/mg.

According to another embodiment of this aspect, multiparticulate composition when administered to healthy subjects under fed conditions provide a mean $AUC_{0-t}$ value in the range of about 12 to about 53 ng·hr/mL/mg.

According to another embodiment of this aspect, the multiparticulate composition has reduced inter-subject variability as compared to marketed extended release tablet of ranolazine.

According to another embodiment of this aspect, the extended release coated cores have $d_{90}$ particle size range from about 0.35 mm to about 0.90 mm determined using a Malvern particle size analyzer.

According to another embodiment of this aspect, the extended release coated cores have $d_{10}$ particle size range from about 0.20 mm to about 0.75 mm determined using a Malvern particle size analyzer.

According to another embodiment of this aspect, the top layer coated cores have $d_{90}$ particle size range from about 0.40 mm to about 1.2 mm determined using a Malvern particle size analyzer.

According to another embodiment of this aspect, the top layer coated cores have $d_{10}$ particle size range from about 0.25 mm to about 0.8 mm determined using a Malvern particle size analyzer.

The term "$d_{90}$ value" as used in the application, means that 90% of the extended release coated cores have a volume diameter in the specified range when measured by a light scattering method such as a Malvern® Mastersizer.

The term "$d_{10}$ value" as used in the application, means that 10% of the extended release coated cores have a volume diameter in the specified range when measured by a light scattering method such as a Malvern® Mastersizer.

According to another embodiment of above aspect, the multiparticulate composition may be filled into a capsule or a sachet.

According to another embodiment of above aspect, the amount of pellets filled in a sachet or capsule can range from about 1.2 g to about 3.0 g for 1000 mg of Ranolazine.

In fifth aspect of the present invention, there is provided an extended release multiparticulate composition comprising a plurality of discrete units, each discrete unit comprising:
a) a drug layered core comprising an inert unit and a drug layer, wherein the drug layer comprises ranolazine and one or more pharmaceutically acceptable excipients;
b) an extended release coating over the drug layered core, wherein the extended release coating comprises cellulose ether and methacrylic acid copolymer, wherein ranolazine is present in said composition in an amount of about 1000 mg, and wherein said composition releases:
about 15% to about 40% of the ranolazine in an initial 2 hours in 900 ml 0.1N HCl, and
releases about 60 to about 80% of the ranolazine in 6 hours in 900 ml pH 6.8 phosphate buffer; when measured in United States Pharmacopoeia (USP) type II dissolution apparatus, rotating at 50 rpm at a temperature of 37° C.

In sixth aspect of the present invention, there is provided a process of preparation of extended-release multiparticulate composition comprising a plurality of discrete units comprising ranolazine, wherein the process comprises:

a) coating inert cores with a solution or dispersion of ranolazine to obtain drug-layer coated cores;
b) coating the drug-layer coated cores of step a) with a solution or dispersion of extended-release polymer to form extended-release coated cores;
c) optionally coating extended-release coated cores of step (b) with a solution or dispersion of top coat polymers to form top coated cores;
d) blend top coated cores of step c) with pharmaceutically acceptable excipients;
e) filling the blend of step (d) into a sachet or hard gelatin capsules of suitable size.

In seventh aspect of the present invention, there is provided a process of preparation of extended-release multiparticulate composition comprising a plurality of discrete units comprising ranolazine, wherein the process comprises:
a) coating inert cores with a solution or dispersion of ranolazine to obtain drug-layer coated cores;
b) coating the drug-layer coated cores of step a) with a solution or dispersion of extended-release polymer to form extended-release coated cores;
c) optionally coating extended-release coated cores of step b) with a solution or dispersion of top coat polymers to form top coated cores;
d) blend top coated cores of step c) with pharmaceutically acceptable excipients;
e) compressing the blend of (d) into mini-tablets and
f) filling the minitablets of step (e) into a sachet or hard gelatin capsules of suitable size.

The multiparticulate composition of present invention may further comprise pharmaceutically acceptable excipients for example binders, diluents, lubricants/glidants, surfactants, sweeteners, anti-tacking agents, opacifiers, anti-foaming agents, coloring agents/flavoring agents or mixtures thereof.

Examples of diluents include, but not limited to, lactose, sorbitol, calcium dihydrogen phosphate dihydrate, calcium phosphate-dibasic, calcium phosphate-tribasic, calcium sulfate, microcrystalline cellulose, silicified microcrystalline cellulose, mannitol, starch, pregelatinized starch, and mixtures thereof.

Examples of binders include, but not limited to, corn starch, pregelatinized starch, microcrystalline cellulose, silicified microcrystalline cellulose, methyl cellulose, hydroxypropyl cellulose (HPC-L), methylcellulose, carboxymethyl cellulose sodium, hydroxypropyl methylcellulose, polyvinylpyrrolidone, and mixtures thereof.

Examples of lubricants and glidants include, but not limited to, colloidal anhydrous silica, stearic acid, magnesium stearate, glyceryl behenate, calcium stearate, sodium stearyl fumarate, stearic acid, talc, microcrystalline wax, yellow beeswax, white beeswax, and mixtures thereof. These may be present in the composition in the range from about 0.01% to about 10% of the total weight of the multiparticulate composition.

Examples of surfactants include, but not limited to, sorbitan monostearate, polyoxythylene sorbitan monostearate, e.g., Polysorbate 60 or Polysorbate 80, non-ethoxylated glyceryl monostearate, cetomacrogol, cetostearyl alcohol, sodium stearoyl lactylate, lecithin, and mixtures thereof. These may be present in the composition in the range from about 0.1% to about 20% w/w of the total weight of the multiparticulate composition.

Examples of sweeteners include, but not limited to, sucrose, sucralose, sorbitol, xylitol, dextrose, fructose, maltitol, acesulfame potassium, aspartame, saccharin, saccharin sodium, glucose, cyclamate, sodium cyclamate, and mixtures thereof. These may be present in the composition in the range from about 0.1% w/w to about 20% w/w of the total weight of the multiparticulate composition.

Examples of opacifiers include titanium dioxide, silicon dioxide, talc, calcium carbonate, behenic acid, and mixtures thereof.

Examples of anti-tacking agents include talc, colloidal silicon dioxide, and mixtures thereof.

Examples of anti-foaming agents include silicon based surfactants, e.g. simethicone; vegetable oils; waxes; hydrophobic silica; polyethylene glycol; and mixtures thereof.

Suitable solvents are selected from the group comprising water, methyl alcohol, ethyl alcohol, isopropyl alcohol, n-butyl alcohol, acetone, acetonitrile, chloroform, methylene chloride, water, and mixtures thereof.

The coloring agents and flavoring agents of the present invention may be selected from any FDA approved colors or flavors for oral use.

Coating may be carried out by using any conventional coating techniques known in the art, such as spray coating in a conventional coating pan, fluidized bed processor, or dry powder coating.

The extended release multiparticulate composition of the present invention can be prepared by various methods including fluidized bed granulation, wet granulation, solvent evaporation, spray drying or combinations thereof.

The term "about" as used herein, refers to any value which lies within the range defined by a variation of up to ±10% of the value.

The term "sprinkle" as used herein refers to extended release multiparticulate composition which is sprinkled on to the soft foods or any edible material or liquids such as apple sauce, yoghurt or drinks, and then administered orally to the patients. The multiparticulate composition may also be administered through feeding tube in patients who cannot swallow.

Bioequivalence is established by comparing pharmacokinetic parameters, for example mean AUC and $C_{max}$ of the present invention with Ranexa® extended release tablets in healthy human subjects.

The term "AUC" refers to the area under the time/plasma concentration curve after the administration of multiparticulate composition of ranolazine to healthy human subjects.

The term "$C_{max}$" refers to the maximum concentration of ranolazine in the blood following the administration of multiparticulate composition of ranolazine to healthy human subjects.

The term "$T_{max}$" refers to the time at which the peak plasma level concentration of ranolazine is attained in a healthy human subjects following administration of multiparticulate composition of ranolazine.

The term "stable" as used herein, refers to a physical stability which means that the extended release coat over the multiparticulate composition retain its structural integrity and does not rupture in a significant way after exposure to acidic environment for the given time period as determined by the drug release and also includes chemically stability which means the multiparticulate composition is stable when stored under the temperature and humidity conditions of 40° C./75% RH and 30° C./65% RH for 6 months.

The Examples are given solely for the purpose of illustration and are not to be construed as limitations of the present invention, as many variations thereof are possible without departing from the spirit and scope of the invention.

EXAMPLES

| Ingredients | % w/w/sachet | |
|---|---|---|
| | Example 1 | Example 2 |
| Drug Layering | | |
| Microcrystalline Cellulose beads | 13.67 | 13.67 |
| Ranolazine | 68.34 | 68.34 |
| Hypromellose | 6.83 | 6.83 |
| Purified water | qs | Qs |
| Isopropyl alcohol | qs | Qs |
| Extended Release Polymer coating | | |
| Ethyl Cellulose | 2.45 | 2.67 |
| Eudragit L100-55 | 5.44 | 5.01 |
| Hypromellose | 1.71 | 1.92 |
| Dibutyl sebacate | 1.07 | 1.07 |
| Isopropyl alcohol | qs | Qs |
| Purified water | qs | Qs |
| Lubrication | | |
| Magnesium Stearate | 0.50 | 0.50 |

Manufacturing Process:
1. Ranolazine and Hypromellose were dispersed in a mixture of purified water and isopropyl alcohol to obtain a dispersion.
2. The dispersion of step 1 was sprayed onto microcrystalline cellulose beads to form ranolazine-coated cores.
3. Ethyl cellulose was dissolved in isopropyl alcohol and purified water.
4. Eudragit L100-55, Hypromellose and dibutyl sebacate were added into the solution of step 3.
5. The dispersion of step 4 was sprayed onto the ranolazine-coated cores of step 2 to obtain extended-release coated cores.
6. The extended-release coated cores of step 5 were lubricated with magnesium stearate.
7. The lubricated extended release coated cores obtained from step 6 were filled into a sachet.

Dissolution Studies:

Dissolution tests were carried out using Example 1 and Example 2. The dissolution was carried out in a USP type II apparatus in 900 mL of 0.1 N HCl for initial 2 hours followed by changeover to pH 6.8 phosphate buffer at 50 rpm, at a temperature of 37° C.±0.5° C. The samples were taken at predefined time points and analyzed by high performance liquid chromatography (HPLC)/UV. The results of the dissolution tests are shown in Table 1.

TABLE 1

Percent drug release of Example 1 and Example 2

| Cumulative Time (hrs) | Cumulative % drug released (Ranolazine) in 0.1N HCl for initial 2 hours followed by changeover media to phosphate buffer pH 6.8 | |
|---|---|---|
| | Example 1 | Example 2 |
| 2 | 37 | 27 |
| 4 | 60 | 51 |
| 6 | 70 | 63 |
| 8 | 77 | 71 |
| 12 | 85 | 77 |

TABLE 1-continued

Percent drug release of Example 1 and Example 2

| Ingredients | % w/w/sachet | |
|---|---|---|
| | Example 3 | Example 4 |
| Drug Layering | | |
| Microcrystalline Cellulose beads | 13.67 | 12.04 |
| Ranolazine | 68.34 | 60.20 |
| Hypromellose | 6.83 | 6.02 |
| Purified water | Qs | Qs |
| Isopropyl alcohol | Qs | Qs |
| Extended Release Polymer coating | | |
| Ethyl Cellulose | 2.66 | 2.93 |
| Eudragit L100-55 | 5.01 | 5.51 |
| Hypromellose | 1.91 | 2.11 |
| Dibutyl sebacate | 1.06 | 1.17 |
| Isopropyl alcohol | Qs | Qs |
| Purified water | Qs | Qs |
| Top coat | | |
| Poly(butyl methacrylate-co-(2-demethylaminoethyl) methacrylate-co-methyl methacrylate) | — | 5.90 |
| Talc | — | 3.09 |
| Isopropyl alcohol | — | Qs |
| Acetone | — | Qs |
| Lubrication | | |
| Talc | — | 0.99 |
| Magnesium Stearate | 0.49 | — |

Manufacturing Process of Example 3:
1. Ranolazine and Hypromellose were dispersed in a mixture of purified water and isopropyl alcohol to obtain a dispersion.
2. The dispersion of step 1 was sprayed onto microcrystalline cellulose beads to form ranolazine-coated cores.
3. Ethyl cellulose was dissolved in isopropyl alcohol and purified water.
4. Eudragit L100-55, Hypromellose and dibutyl sebacate were added into the solution of step 3.
5. The dispersion of step 4 was sprayed onto the ranolazine-coated cores of step 2 to obtain extended-release coated cores.
6. The extended release coated cores of step 5 were lubricated with magnesium stearate and filled into a sachet, Manufacturing Process of Example 4:
1. Ranolazine and Hypromellose were dispersed in a mixture of purified water and isopropyl alcohol to obtain a dispersion.
2. The dispersion of step 1 was sprayed onto microcrystalline cellulose beads to form ranolazine-coated cores.
3. Ethyl cellulose was dissolved in isopropyl alcohol and purified water.
4. Eudragit L100-55, Hypromellose and dibutyl sebacate were added into the solution of step 3.
5. The dispersion of step 4 was sprayed onto the ranolazine-coated cores of step 2 to obtain extended-release coated cores.
6. Poly(butyl methacrylate-co-(2-demethylaminoethyl) methacrylate-co-methyl methacrylate) and talc were added to the solution of isopropyl alcohol and acetone.
7. The extended-release coated cores of step 5 were coated with solution of step 6.
8. The coated cores of step 7 were lubricated with magnesium stearate and filled into a sachet.

TABLE 3

Percent drug release of Example 3 and Example 4

| Cumulative Time (hrs) | Cumulative % drug released (Ranolazine) in 0.1N HCl for initial 2 hours followed by changeover media to phosphate buffer pH 6.8 | |
|---|---|---|
| | Example 3 | Example 4 |
| 2 | 27 | 31 |
| 4 | 51 | 59 |
| 6 | 63 | 71 |
| 8 | 71 | 77 |
| 12 | 77 | 83 |

Pharmacokinetic Studies Under Fasting and Fed Conditions

The extended release multiparticulate composition of ranolazine in Example 4 is compared with Ranexa® extended release tablets under fasting and fed condition in 11 healthy adult human subjects.

Values for various pharmacokinetic parameters, including observed mean $C_{max}$, $AUC_{0-t}$ and $AUC_{0-\infty}$ were calculated for Example 4 and are provided in Table 4 below.

TABLE 4

| Pharmacokinetic parameters (N = 12) | Fasting | Fed |
|---|---|---|
| Mean $T_{max}$ (hours) | 6.04 | 6.25 |
| Mean $C_{max}$ (ng/mL/mg) | 1.77 | 2.62 |
| Mean $AUC_{0-t}$ (ng · hr/mL/mg) | 24.165 | 28.233 |
| Mean $AUC_{0-\infty}$ (ng · hr/mL/mg) | 24.434 | 28.417 |

The invention claimed is:

1. An extended release multiparticulate composition comprising a plurality of discrete units, each discrete unit comprising:
   a) a drug layered core comprising an inert core and a drug layer, wherein the drug layer comprises ranolazine and one or more pharmaceutically acceptable excipients;
   b) an extended release coating over the drug layered core, wherein the extended release coating comprises a mixture of a water-insoluble polymer and a pH-dependent polymer, wherein said water-insoluble polymer and pH-dependent polymer are present in a weight ratio of from about 1:2 to about 1:3;
   wherein said multiparticulate composition releases:
   about 15% to about 40% of the ranolazine in an initial 2 hours in 900 mL 0.1N HCl and releases about 60% to about 90% of the ranolazine in 6 hours in 900 mL pH 6.8 phosphate buffer; when measured in United States Pharmacopoeia (USP) type II dissolution apparatus, rotated at 50 rpm at a temperature of 37° C.;
   wherein the composition is filled into a capsule or a sachet and the composition comprises about 1000 mg of ranolazine and wherein ranolazine is present in an amount of about 40% to about 85% by weight of the multiparticulate composition.

2. The extended release multiparticulate composition of claim 1, wherein said discrete units are in a form selected from the group consisting of pellets, granules, minitablets and beads.

3. The extended release multiparticulate composition of claim 1, wherein said discrete units further comprise a top coat.

4. The extended release multiparticulate composition of claim 1, wherein said water-insoluble polymer is selected from the group consisting of cellulose ethers, cellulose esters, polymethacrylic acid ester copolymers, aminoalkyl methacrylate copolymers, a copolymer of polyvinyl acetate and polyvinylpyrrolidone, and mixtures thereof.

5. The extended release multiparticulate composition of claim 1, wherein said pH-dependent polymer is selected from the group consisting of methyl acrylate acrylic acid copolymer, methyl acrylate methacrylic acid copolymer, butyl acrylate styrene acrylic acid copolymer, methacrylic acid methyl methacrylate copolymer, methacrylic acid ethyl acrylate copolymer methyl acrylate methacrylic acid octyl acrylate copolymer; hydroxypropylmethylcellulose acetate succinate, hydroxypropylmethylcellulose phthalate, hydroxymethylethylcellulose phthalate, cellulose acetate phthalate, cellulose acetate succinate, cellulose acetate maleate, cellulose acetate trimelliate cellulose benzoate phthalate, cellulose propionate phthalate, methylcellulose phthalate, carboxymethylethylcellulose, ethylhydroxyethylcellulose phthalate, polyvinyl alcohol phthalate, polyvinylacetal phthalate, polyvinyl butylate phthalate, polyvinylacetoacetal phthalate, maleic acid copolymers and mixtures thereof.

6. The extended release multiparticulate composition of claim 1, wherein said water-insoluble polymer is cellulose ether and wherein said pH dependent polymer is methacrylic acid copolymer.

7. The extended release multiparticulate composition of claim 1, wherein said extended release coating layer further comprises a plasticizer selected from the group consisting of acetyl tributyl citrate, acetyl triethyl citrate, dibutyl sebacate, diethyl phthalate, castor oil, diacetylated monoglycerides, triacetin, tributyl citrate, triethyl citrate and mixtures thereof.

8. The extended release multiparticulate composition of claim 1, wherein the drug layer comprises about 50% to about 70% of ranolazine by total weight of the multiparticulate composition.

9. The extended release multiparticulate composition of claim 1, wherein the drug layer comprises about 60% to about 80% of ranolazine.

* * * * *